United States Patent [19]

Failli et al.

[11] Patent Number: 4,529,731

[45] Date of Patent: Jul. 16, 1985

[54] THIADIAZOLEDIAMINE DERIVATIVE WITH HISTAMINE H-2 RECEPTOR INHIBITING PROPERTIES

[75] Inventors: Amedeo Failli, St. Laurent; Luis Borella, Beaconsfield, both of Canada

[73] Assignee: American Home Products Corporation, New York, N.Y.

[21] Appl. No.: 534,953

[22] Filed: Sep. 22, 1983

[51] Int. Cl.³ .................. A61K 31/445; C07D 417/12
[52] U.S. Cl. ...................................... 514/326; 546/209
[58] Field of Search ........................ 546/209; 424/267

[56] References Cited

U.S. PATENT DOCUMENTS

| 4,374,248 | 2/1983 | Crenshaw et al. | 548/135 |
| 4,380,638 | 4/1983 | Crenshaw et al. | 548/135 |
| 4,380,639 | 4/1983 | Crenshaw et al. | 548/135 |

FOREIGN PATENT DOCUMENTS

| 0040696 | 12/1981 | European Pat. Off. | 548/135 |
| 2067987A | 8/1981 | United Kingdom | 548/135 |

Primary Examiner—Robert T. Bond

[57] ABSTRACT

N-[2-(dimethylamino)ethyl]-N'-[3-[3-[(1-piperidinyl)-methyl]phenoxy]-propyl]-1,2,5-thiadiazole-3,4-diamine, 1-oxide is a long acting histamine H-2 receptor antagonist. The compound inhibits gastric acid secretion, and prevents and alleviates ulcers.

14 Claims, No Drawings

THIADIAZOLEDIAMINE DERIVATIVE WITH HISTAMINE H-2 RECEPTOR INHIBITING PROPERTIES

BACKGROUND OF THE INVENTION

This invention relates to N-[2-dimethylamino)ethyl]-N'-[3- [3-[(1- piperidinyl)methyl]phenoxyl]propyl]-1,2,5-thiadiazole-3,4-diamine, 1-oxide, the object compound of this invention. The object compound has the following formula:

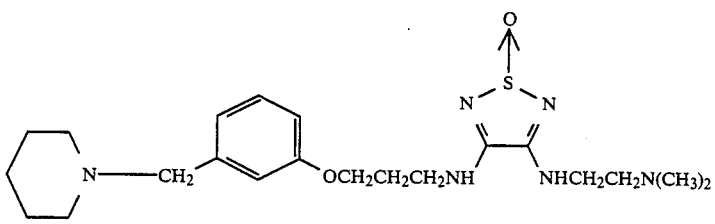

The invention also relates to a process for preparing the compound, to a pharmaceutical formulation thereof, and to methods of using the compound.

R. R. Crenshaw and A. A. Algieri, U.K. Patent Application No. 2,067,987 A, published Aug 5, 1981, and J. J. Baldwin et al., European Patent Application NO. 81102976.8, published Dec. 2, 1981, disclose a number of specific 3,4-disubstituted 1,2,5-thiadiazole-3,4diamine, 1-oxides as inhibitors of gastric acid. The inhibitors function by inhibiting the histamine H-2 receptors. Although N-[2-(dimethylamino)ethyl]-N'-[3-[3-[(1-piperidinyl]methyl]phenoxy ]propyl]- 1,2,5-thiadiazole-3,4-diamine, 1-oxide can be constructed from the generic teachings, it is not exemplified in the numerous examples contained in the above two patents.

We have found N-[2-(dimethylamino)ethyl]-N'-[3-[3-[(1-piperidinyl)- methyl]phenoxy]propyl]-1,2,5-thiadiazole-3,4-diamine, 1-oxide to be an effective inhibitor of histamine H-2 receptors. Investigations with the compound further show that the compound has a specificity of inhibiting gastric acid secretion.

Furthermore, and unexpectedly, the compound has been found to have long acting properties. Consequently, the compound is most suitable as the active ingredient for a "once-a-day" pharmaceutical formulation. These properties, along with a relatively low order of toxicity, render N-[2-(dimethylamino)ethyl] -N'-[3- [3-[(1-piperidinyl)methyl]phenoxyl]propyl]-1,2,5-thiadiazole- 3,4-diamine, 1-oxide as a valuable agent for reducing excesses of gastric acid secretion and for treating ulcers in humans and animals.

SUMMARY OF THE INVENTION

The object compound, N-[2-(dimethylamino)ethyl]-N'-[3-[3-[(1- piperidinyl)methyl]phenoxy]propyl]-1,2,5-thiadiazole-3,4-diamine, 1-oxide, specifically inhibits H-2 histamine receptors. The compound is an effective agent for reducing gastric acid scretion and for treating gastrointestinal ulcers in a mammal.

When an H-2 histamine receptor inhibiting amount of the compound is combined with a pharmaceutically acceptable carrier, a long acting pharmaceutical formulations is obtained.

A process for preparing the object compound is disclosed hereinafter.

DETAILS OF THE INVENTION

When the object compound of this invention is administered to a mammal, for example, a human, rabbit or rat, suffering from hyperchlorhydria and/or associated conditions for the purpose of preventing or decreasing the secretion of excessive amount of gastric acid or hydrochloric acid, or is used for the treatment of ulcers in mammals, it is used alone or in combination with pharmacologically acceptable carriers, the proportion of which is determined by the solubility and chemical nature of the compound, chosen route of administration and standard biological practice.

For example, the compound can be administered orally in solid form i.e. capsule or tablet, orally in liquid form, i.e. suspensions or solutions, or it can be injected parenterally. The preferred method of administration is oral.

The tablet compositions can contain the compound in admixture with pharmaceutically acceptable excipients, for example, starch, milk, sugar etc. The tablets can be uncoated, or optionally they can be coated by known techniques so as to delay disintegration and adsortion in the gastrointestinal tract and thereby provide an even more sustained action over a longer period.

The aqueous suspensions for oral administration can contain the compound in admixture with one or more nontoxic pharmaceutical excipients known to be suitable in the manufacture of aqueous suspensions. Suitable excipients are, for example, methylcellulose, sodium alginate, gum acacia, lecithin, etc. The aqueous suspensions can also contain one or more preservatives, one or more coloring agents, one or more flavoring agents or one or more sweetening agents.

Non-aqueous suspensions for oral administration can be formulated by suspending the compound in a vegatable oil, for example, arachis oil, olive oil, sesame oil, or coconut oil, or in liquid paraffin, and the suspension may contain a thickening agent, for example, beeswax, hard paraffin or cetyl alcohol. These compositions can also contain a sweetening agent, flavoring agent or antioxidant.

For administration to a mammal by parenteral injection, it is preferred to use the compound in solution in a sterile aqueous vehicle, which may also contain other solutes such as buffers or preservatives, as well as sufficient quantities of pharmaceutically acceptable salts or of glucose to make the solution isotonic.

The dosage of the compound for combating or preventing hyperchlorhydria and/or associated conditions, or for the treatment of ulcers, in a mammal will vary with the form of administration and the particular compound chosen. Furthermore, it will vary with the particular host as well as the age, weight and condition of the host under treatment as well as the nature and extent of the symptoms. Generally, treatment is initiated with small dosages substantially less than the optimum dose of the compound. Thereafter, the dosage in increased by small increments until the optimum effect under circumstances is reached. In general, the compound is most desirably administered at a concentration level that will generally afford effective results without causing any harmful or deleterious side effects. For example, an effective antiulcer amount, or an effective amount for preventing hyperchlorhydria and inhibiting hydrochloric acid secretion, of the compound usually ranges from about 10 mg to about 100 mg per kg of body weight per day in single dose, although as aforementioned, variations will occur. However, a dosage level that is in the range from about 10 mg to about 50 mg per kg of body weight per day in single or divided dose is employed most desirably in order to achieve effective results.

Unit dosage forms such as capsules, tablets, syrups, suspensions and the like may contain from 10 mg to about 100 mg of the active agent of this invention with a pharmaceutical carrier.

The effectiveness of the compound as an agent for preventing hyperchlorhydria and inhibiting gastric acid secretion can be demonstrated readily in pharmacological test. For example, the following test demonstrates their effectiveness in inhibiting spontaneous gastric acid secretion in cannulated rats.

Male albino Sprague Dawley rats (200–300 g), purchased from Canadian Breeding Laboratories, were employed. Two gastric cannulas were implanted surgically in each rat as described by L. E. Borella and F. Herr, Gastroenterology, 61, 345 (1971). The rats were used two to three weeks after the operation at a time when their food intake and weight gain were similar to the food intake and weight gain of unoperated litter mates. Before testing, the rats were deprived of food for 18 hours, but they had available a solution of 0.2% sodium chloride in 5% glucose for drinking ad libitum. Prior to each experiment, the plugs of the stomach cannulas of each rat were removed and the debris present in the stomach was flushed out with tepid saline passed through the cannulas. Thereafter, the lumen of the stomach was continuously perfused with saline introduced into the stomach through the forestomach cannula at a rate of 0.8–1.2 ml/min. The stomach perfusate flowing out of the antrum cannula was collected in 60 minutes intervals and the total acid in each collection was titrated with 0.05 N sodium hydroxide employing phenol red as an indicator. After a period of acclimatization of about 60 to 90 minutes, the acid output values were recorded. On the basis of the hourly acid output, the rats were divided into equal groups so that the average acid output of all groups was similar. Saline (vehicle) or saline suspensions or solutions of the test compounds were administered intragastrically (i.g.) through the forestomach cannula, after having closed the antral cannula. During the one hour absorption period, the stomachs of the rats were not perfused. After the absorption period, perfusion of the stomachs was resumed, and the perfusates were collected hourly for three hours. The average post-treatment hourly acid outputs of the test compound groups were compared to that of the saline group and the percent inhibition of acid output was calculated. Multiple statistical comparisons between groups was done using Dunnet's test, C. W. Dunnet, Journal of American Statistical Association, 50, 1096 (1955).

Results obtained, when N-[2-(dimethylamino)ethyl]-N'- [3-[3-[(1-piperidinyl)methyl]phenoxy]propyl]-1,2,5- thiadiazole-3,4-diamine, 1-oxide, was tested according to the preceding method, are shown in the following table.

| PERORAL DOSE IN mg/kg OF OBJECT COMPOUND | % INHIBITION OF 3 HOURS GASTRIC ACID OUTPUT |
| --- | --- |
| 20 | 36 |
| 40 | 65 |
| 80 | 74 |

The long acting inhibiting effect of the object compound on gastric acid secretion can be demonstrated in the preceding test. The results shown in the following table were obtained after a peroral dose of 80 mg/kg of N-[2-(dimethylamino)ethyl]-N'-[3-[3-[(1-piperidinyl)-methyl]phenoxy]propyl]-1,2,5- thiadiazole-3,4-diamine, 1-oxide; 80 mg/kg of cimetidine and 60 mg/kg of ranitidine. the latter two compounds are commercially important histamine H-2 receptor anatagonists.

| TEST COM-POUND | % INHIBITION OF ACID OUTPUT AT VARIOUS TIMES(HR) AFTER DOSING | | | | | | | | | | | | |
| --- | --- | --- | --- | --- | --- | --- | --- | --- | --- | --- | --- | --- | --- |
| | 1 | 2 | 3 | 4 | 5 | 6 | 7 | 8 | 9 | 10 | 18 | 19 | 20 |
| Object | 88 | 95 | 96 | 95 | 94 | 85 | 61 | 52 | 63 | 64 | 32 | 29* | 7 |
| cimetidine | 84 | 84 | 63 | 52* | 3 | | | | | | | | |
| ranitidine | 69 | 81 | 65 | 63 | 44* | 39 | 6 | | | | | | |

*Last statistically significant value

The above comparison shows that peroral doses of 80 mg/kg and 60 mg/kg, respectively, of cimetidine and ranitidine cease to show a significant response after 5 and 6 hours, respectively; as contrasted to the longer acting effect of N-[2-(dimethylamino)ethyl]-N'-[3-[3-[(1-piperidinyl)methyl]phenoxy]propyl]-1,2,5-thiadiazole-3,4-diamine, 1-oxide.

The beneficial effect of the object compound on gastrointestinal ulcer formation can be demonstrated by assessing its effect on the development of cold-restraint-induced gastric lesions according to a modified method of by E. C. Senay and R. J. Levine, Proc. Soc. Exp. Biol. Med., 124, 1221 (1967).

More explicitly exemplified, the beneficial effects were evaluated as follow: Food was withheld from male albino rats (165–175 g, Sprague-Dawley, Canadian Breeding Laboratories) for 24 hours but water was freely available. The object compound was administered orally in one milliliter of a liquid vehicle to the animals 30 minutes before placing the animals into restrainers. Just prior to being restrained, each animal was given orally 50 mg of sodium taurocholate. The vehicle empoloyed was saline containing polysorbate 80 (oleate ester of sorbitol and its anhydrides copolymerized with ethylene oxide), one drop per five milliliters of saline. The restrainers were made of plexiglass and restricted the movement of the rat to a minimum. The restrainers were placed in a cold environment (4°–5° C.) for three hours. The animals were sacrificed by cervical dislocation, the stomachs removed and the number of ulcers in the glandular portion of the stomach determined. Results are given in the following table.

| TREATMENT (mg/kg, p.o.) | NO. OF RATS | ULCER SCORE (MEAN ± S.E.) | % INHIBITION |
| --- | --- | --- | --- |
| Saline | 19 | 19 ± 4 | — |
| Object | 11 | 10 ± 9 | 44 |

-continued

| TREATMENT (mg/kg, p.o.) | NO. OF RATS | ULCER SCORE (MEAN ± S.E.) | % INHIBITION |
|---|---|---|---|
| Compound (1) Object | 9 | 2 ± 1 | 89* |
| Compound (5) Object Compound (20) | 9 | 0.9 ± 0.5 | 95** |

*p < 0.05
**p < 0.01

The object compound of this invention can be prepared by reacting a starting material of formula

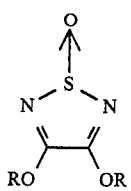

wherein R is lower alkyl containing one to three carbon atoms stepwise with equimolar amounts of 3-[3-(1-piperidinylmethyl)phenoxy]-N-propylamine and 2-(dimethylamino)ethylamine.

The following is an exemplification of the process:

A solution of 3,4-diethoxy-1,2,5-thiadiazole-oxide (7.65 g, 40.26 mmole), described by J. S. Amato et al., J. Amer. Chem. Soc., 104, 1375 (1982), was added dropwise at 20-22° C. to a stirred solution of 3-[3-(1-piperidinylmethyl)phenoxyl]-N-propylamine (10 g, 40.26 mmole), described in Glaxo Group Limited's Belgian Pat. No. 875,846, granted Oct. 25, 1979, in ethanol (1.5 L). After the addition, the reaction mixture was stirred for 1 hr at 20-22° C. The solvent was evaporated from the reaction mixture. The residue was dissolved in chloroform. The chloroform solution was dried (MgSO4) and then evaporated to dryness. The residue was placed on a column of 400 g of silica gel.

The column was washed with chloroform. Subsequent elution with chloroform-methanol (98:2, v/v) gave 13.2 g (83.5%) of 3-ethoxy-4-[[3[3-(1- piperidinylmethyl)phenoxy]propyl]amino]-1,2,4-thiadiazole, 1-oxide; NMR (CDCl3) δ1.5 (t, J×7Hz, 3H), 1.5 (broad, 6H), 2.25 (m, 6H), 3.4 (s, 2H), 3.7 (m, 2H), 4.1 (t, J=6Hz, 2H), 455 (q, J=7Hz, 2H), 6.55 (broad, 1Hl, 7.0 (m, 4H). The latter compound (2.7 g, 6.88 mmole) was dissolved in acetonitrile (80 mL). 2-(Dimethylamino)ethylamine (0.66 g, 0.82 mL, 7.48 mmole) was added to the solution. The reaction mixture was stirred for 2 hr at 20 ° to 22° C. The solvent was evaporated from the reaction mixture and the residue was placed on a column of 100 g of silica gel. Elution with chloroform-methanol-concentrated ammonium hydroxide (97.4: 12:0.6, v/v/v) gave 1.5 g (50%) of a beige oil which slowly crystallized under diethyl ether. Recrystallization of the crystalline material from ethyl acetate gave N-[2 -dimethylamino)ethyl]- N'-[3-[3[(1- piperidinyl)-methyl]phenoxy]propyl]-1,2,5-thiadiazole-3,4-amine, 1-oxide—the object compound of this invention; mp 95°-99° C,IR(CHCl3) δ3280, 3120, 1610, 1045 cm⁻¹; NMR (CDCl3) δ1.50(m,6H), 2.25(s, 6H), 2.35 (m, 8H), 3.4 (s, 2H), 3.5 (m, 4H), 4.0 (t, J=5.5Hz, 2H), 7.0 (m, 4H), 8.1 (broad, 1H).

We claim:

1. N-[2-(Dimethylamino)ethyl]-N'-[3-[3-[(1-piperidinyl)methyl]phenoxy]propyl]- 1,2,5-thiadiazole-3,4diamine, 1-oxide.

2. A method of inhibiting H-2 histamine receptors in a mammal in need of inhibition of said receptors, which comprises: administering to said mammal an effective amount of the compound of claim 1 to inhibit said receptors.

3. The method of claim 2 wherein the amount of compound ranges from 10 mg to 100 mg per kg of body weight per day.

4. The method of claim 2 wherein the amount ranges from 10 mg to 50 mg per kg of body weight per day.

5. A method for preventing or treating gastrointestinal ulcers in a mammal, which comprises administering to the mammal in need thereof an effective amount of the compound of claim 1.

6. The method of claim 5 wherein the amount of compound ranges from 10 mg to 100 mg per kg of body weight per day.

7. The method of claim 5 wherein the amount ranges from 10 mg to 50 mg per kg of body weight per day.

8. A method for preventing or decreasing the secretion or availability of excessive amounts of gastric acid in a mammal suffering from hyperchlorhydria, which comprises administering to the mammal in need thereof an effective amount of the compound of claim 1.

9. The method of claim 8 wherein the amount of compound ranges from 10 mg to 100 mg per kg of body weight per day.

10. The method of claim 8 wherein the amount ranges from 10 mg to 50 mg per kg of body weight per day.

11. A pharmaceutical composition in unit dosage form for inhibiting H-2 histamine receptors comprising N-[2-(dimethylamino)ethyl]-N '-[3-[3[(1- piperidinyl)-methyl]phenoxy]propyl]-1,2,5-thiadiazole-3,4-diamine, 1-oxide and a pharmaceutically acceptable carrier.

12. The pharmaceutical dosage form of claim 11 for preventing or treating gastrointestinal ulcers in a mammmal.

13. The pharmaceutical dosage form of claim 11 for suppressing gastric acid scretions in a mammal.

14. A process for preparing N-[2-(dimethylamino)ethyl]-N'-[3-[3- [(1-piperidinyl)methyl]phenoxy]propyl]-1,2,5-thiadiazole-3,4-diamine, 1-oxide, which comprises:
reacting a compound of formula

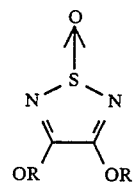

wherein R is lower alkyl containing one to three carbon atoms with 3[3-(1- piperidinylmethyl)phenoxy]-N-propylamine to obtain 3-(lower alkoxy)-4-[[3- [3-(1-piperidinylmethyl)phenoxy]propyl]aminol]-1,2,5-thiadiazole, 1-oxide, wherein the lower alkoxy contains one to three carbon atoms; and reacting the latter compound with 2-(dimethylamino)ethylamine.

* * * * *